United States Patent [19]
Owens et al.

[11] Patent Number: 6,110,410
[45] Date of Patent: Aug. 29, 2000

[54] METHOD OF MAKING A DISPOSABLE CASSETTE WITH NEGATIVE HEAD HEIGHT FLUID SUPPLY

[75] Inventors: Dana J. Owens, Irving; Aaron Raines, Dallas; Ed G. Rasmussen; David J. Harrison, both of Carrollton; Carl R. Anderson, Dallas; David G. Ozinga, Flower Mound, all of Tex.

[73] Assignee: McGaw, Inc., Carrollton, Tex.

[21] Appl. No.: 08/711,514

[22] Filed: Sep. 10, 1996

Related U.S. Application Data

[62] Division of application No. 08/282,275, Jul. 27, 1994, Pat. No. 5,554,013, which is a continuation of application No. 08/226,174, Apr. 12, 1994, abandoned, which is a continuation of application No. 07/877,618, May 1, 1992, Pat. No. 5,302,093.

[51] Int. Cl.[7] .................................................. B29C 65/04
[52] U.S. Cl. ..................... 264/491; 156/274.4; 156/275.1
[58] Field of Search ......................... 264/491; 156/275.1, 156/274.4, 380.4, 380.6

[56] References Cited

U.S. PATENT DOCUMENTS

| | | | |
|---|---|---|---|
| 2,747,646 | 5/1956 | Lippman | 156/275.1 |
| 3,655,477 | 4/1972 | Scholl et al. | 156/273 |
| 4,236,880 | 12/1980 | Archibald | 417/478 |
| 4,657,609 | 4/1987 | Hensler | 156/70 |

*Primary Examiner*—Jan H. Silbaugh
*Assistant Examiner*—Stefan Staicovici
*Attorney, Agent, or Firm*—John W. Montgomery; Gardere & Wynne, L.L.P.

[57] ABSTRACT

A method of radio frequency (RF) welding of a flexible PVC sheet to a rigid copolyester carrier by holding a flexible PVC sheet and a rigid copolymer carrier together between heated RF dies. A predetermined temperature differential is maintained between the RF dies, with the flexible sheet side at a higher temperature than the rigid carrier side and adjusted so that a weld plane is established along the interface between the PVC and the copolyester. An RF weld signal is passed through the first and second RF dies and the PVC and copolyester therebetween, so that the flexible PVC sheet and the copolyester rigid carrier partially melt and become welded together at the weld plane.

1 Claim, 12 Drawing Sheets

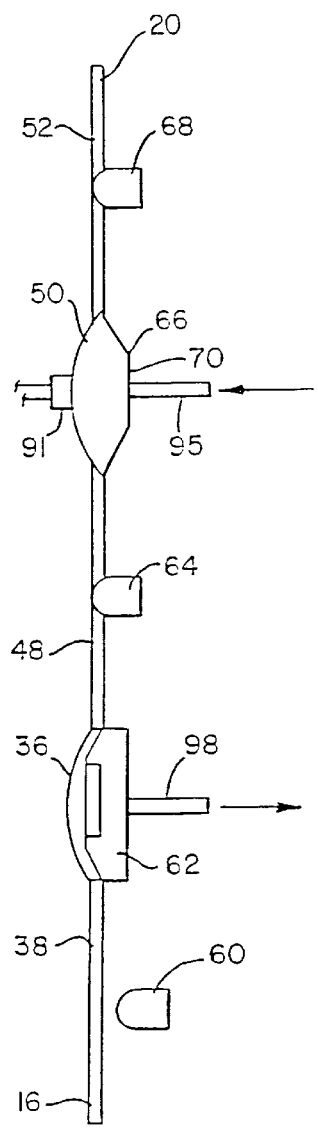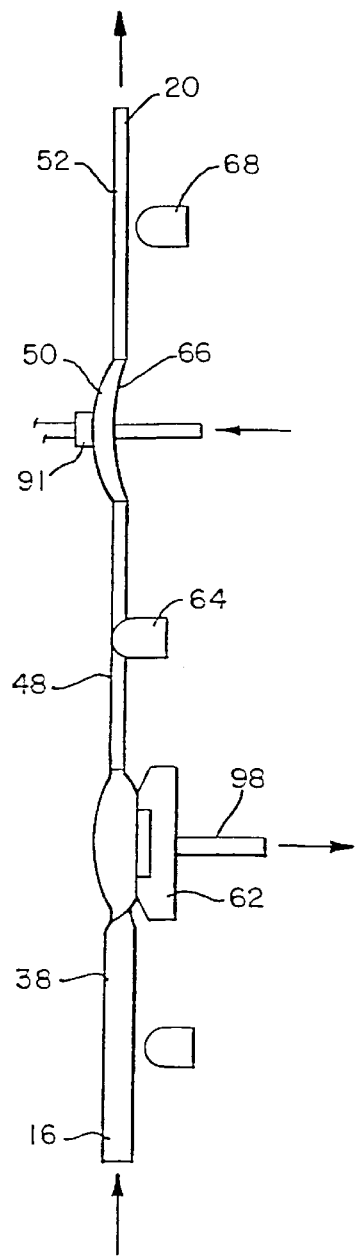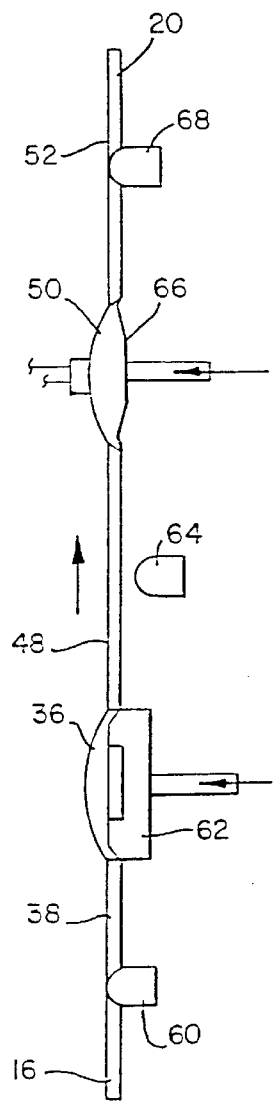

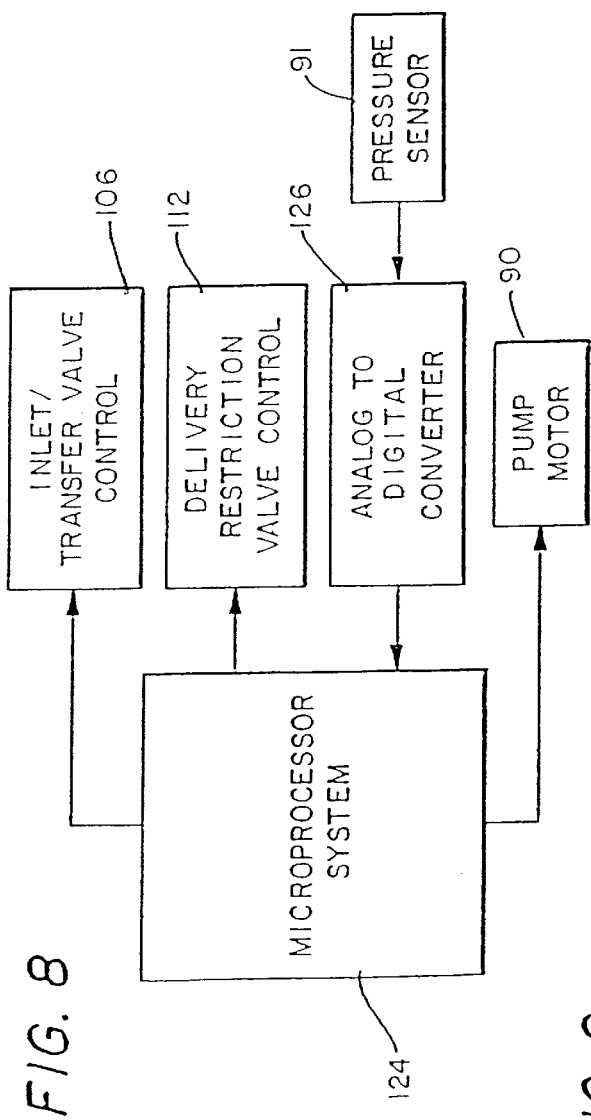

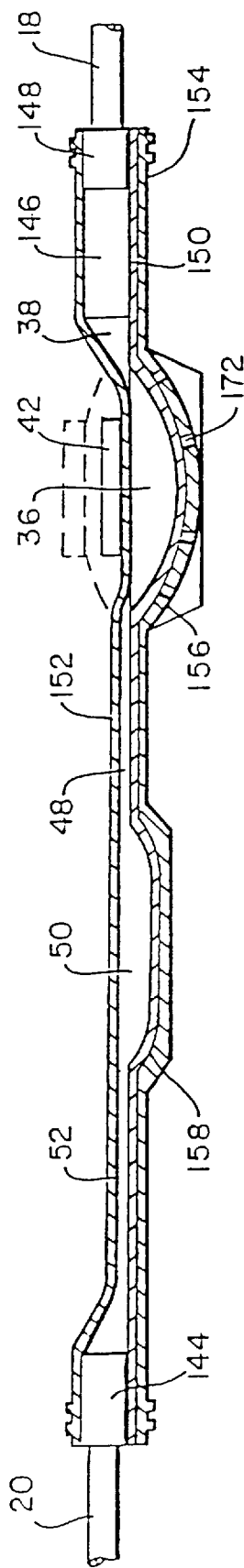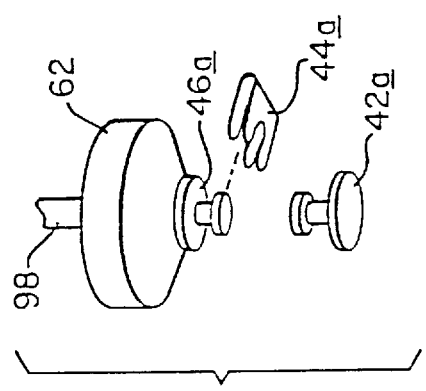

METHOD OF MAKING A DISPOSABLE CASSETTE WITH NEGATIVE HEAD HEIGHT FLUID SUPPLY

CROSS-REFERENCE TO RELATED APPLICATIONS

This with is a divisional of application Ser. No. 08/282,275, filed on Jul. 27, 1994, entitled Disposable Cassette With Negative Head Height Fluid Supply, now U.S. Pat. No. 5,554,013, which is a continuation application of U.S. patent application Ser. No. 08/226,174, filed Apr. 12, 1994, now abandoned, which is a continuation of prior U.S. patent application, Ser. No. 07/877,618, filed May 1, 1992, issued as U.S. Pat. No. 5,302,093.

TECHNICAL FIELD OF THE INVENTION

This invention relates to the delivery of a fluid to a patient by pressurizing the fluid, and in particular, to an infusion pump which provides fluid from a negative head pressure supply for delivery to a patient, which infusion pump incorporates an inexpensive disposable cassette.

BACKGROUND OF THE INVENTION

Infusion of fluids, such as drugs and plasma, into a patient is commonplace in the medical field. Two common infusion methods are intravenous delivery of fluids by gravity and either intravenous or intra-arterial delivery by actually pumping the fluids for delivery to the patient.

In pump delivery, an infusion pump is used to pressurize the fluid. Past devices often require a complex cassette mechanism which comes into direct contact with the fluid to be delivered. Other devices require fluid to be fed by gravity to a pumping instrument having a cassette.

Peristaltic pumps acting upon in-line tubing segments have been used in this art. One example of a peristaltic pump, disclosed in U. S. Pat. No. 4,155,362, includes a back pressure valve to prevent gravity siphoning from the pumping chamber.

Another relatively simple pumping arrangement is disclosed in U. S. Pat. No. 4,142,524, in which a cassette is provided with inlet and outlet valves to and from a pumping chamber. The pump presses a rubber diaphragm on the cassette to diminish the volume of the cassette chamber by a known amount to deliver a predetermined quantity per pump stroke. An even simpler disposable element is disclosed in the pumping arrangement of U.S. Pat. No. 4,199,307, in which a pancake-shaped resilient pumping chamber is provided with upper and lower valves and an activating pumping piston which displaces a known volume on the pumping stroke. Yet another pump approach is disclosed in U.S. Pat. No. 4,322,201, which seeks to provide continuous, uninterrupted fluid flow by alternating between two pumping chambers, each of which employs the principle of the rolling diaphragm. A third rolling diaphragm chamber is employed for mechanically sensing pressure within the device for control purposes.

Another delivery pump system as disclosed in U.S. Pat. No. 4,657,490, employs a simple disposable element in combination with a relatively straightforward gravity supply and positive pumping action which is accurate and which provides pressure monitoring and self-checking diagnostics through measuring the pressure exerted on the pump actuator.

None of the foregoing art, however, provide a simple disposable element with a positive feed capable of drawing fluid from a negative head pressure supply in combination with simple straightforward delivery pumping action which is accurate and reliable and which provides improved reliability pressure monitoring through the cassette pumping membrane and self-check diagnostics.

SUMMARY OF THE INVENTION

One aspect of the present invention is a disposable cassette for use in medical infusion fluid pumping to positively draw fluid into the cassette for positive pumping to a patient. At least one pumping chamber in the cassette cooperates with a pumping instrument (in which it is operatively held) to draw fluid from a negative pressure fluid source or a negative head height without relying on positive head height gravity feed. The cassette is formed of one or two layers of flexible sheet material welded together and applied to a semi-rigid thin backing plate. Detachable connector means are provided in the area of the inlet chamber for drawing in fluid, which connector means are coupled to an actuator in the pumping instrument to which the cassette is inserted. The actuator is detachably coupled to the inlet chamber and upon retraction draws one wall of the chamber away from the other wall, thereby creating a negative pressure within the chamber to draw fluid through the inlet into the chamber. The inlet is closed with a first valve means pressing the inlet closed and the actuator advances against the chamber to decrease the volume of the chamber, forcing out fluid for eventual infusion to the patient. The positive supply of fluid allows a reliable amount of fluid to be available for infusion to the patient whether or not a supply source is above or below the infusion pump. The valve by which fluid is transferred out of the inlet chamber is closed, the inlet valve is opened, and the inlet actuator is withdrawn, so that the inlet chamber walls are moved back creating an increased volume and therefore, a negative pressure in the inlet chamber. The inlet chamber fills with fluid and the cycle can be repeated. When service to the patient is completed, or when the medicine is changed, the inlet actuator can be detached from the inlet chamber and the cassette can be removed and disposed while the relatively more complex pumping and mechanical valve system and instrument can be re-used without contamination. A new sterile cassette can be replaceably inserted and the inlet actuator can be coupled to the inlet chamber for use with a new patient or with a new infusion solution.

Another feature of the invention is the use of a magnetic coupling between the inlet chamber of the cassette and the inlet pumping actuator. A thin metal disk is attached to a flexible wall of the inlet pumping chamber which corresponds in location to a magnetic inlet actuator in the pumping instrument. The magnetic actuator secures itself to a flexible wall through magnetic coupling. The other wall of the inlet chamber of the disposable cassette is rigidified or otherwise restrained from moving toward the flexible wall. In the case of a single flexible sheet, the rigid carrier itself forms the rigidified wall. In the case of two flexible cassette construction, one of these flexible sheets is adhered to the rigid carrier. This allows the inlet pumping actuator to draw the flexible wall outward, thereby increasing the volume within the pumping chamber and drawing fluid into the cassette.

In accordance with another aspect of the present invention, a pumping chamber is provided in the disposable cassette which is distinct from the inlet chamber. Fluid is drawn into the inlet chamber which acts as a reservoir supply chamber or a refill chamber and is transferred from the inlet chamber into the outlet pumping chamber and is pumped to a patient for infusion. The disposable cassette has a flexible wall and a rigid wall defining the inlet and outlet chambers within the cassette the inlet pumping chamber being variable in volume by the retraction or advancement of an inlet actuator, the outlet pump chamber being variable in volume as fluid fills the chamber or is pushed from it with an outlet actuator. The disposable cassette further has an inlet passage for movement of fluid into the inlet pump chamber, a transfer passage for moving fluid from the inlet pump chamber to the outlet pump chamber and an outlet passage for moving the fluid out of the outlet pump chamber. Also, inlet and outlet valves are provided for opening and closing the inlet and outlet, and a transfer valve is provided for opening and closing the transfer passage between the inlet pump chamber and the outlet pump chamber to control movement into the inlet pump chamber and from the inlet pump chamber into the outlet pump chamber. A carrier which is relatively rigid with respect to the flexible wall has an inlet concave depression, which forms a rigid wall spaced apart from the flexible wall of the cassette to form the inlet pumping chamber. Together, the flexible wall and the concave depression establish the inlet chamber volume. The flexible layer is securely affixed around the perimeter edge of the inlet concave depression, such that it is deformable in both inward and outward directions. An inlet pumping actuator is provided for contacting and detachably coupling with the outer surface of the deformable sheet to deform the sheet by either compression or expansion between the deformable sheet and the inlet concave depression and to thereby decrease or increase the volume of the inlet pumping chamber and to draw fluid into the inlet pumping chamber or to expel fluid into the outlet pumping chamber.

An outlet concave depression is defined in the relatively rigid carrier such that the outlet pumping chamber conforms to the outlet concave depression, and is confined in its movement at least in the outward direction.

An outlet pumping actuator is provided for contacting the outer surface of the deformable sheet at the outlet pumping chamber to deform the second sheet between the pumping member and the confining depression of the relatively rigid carrier to decrease the volume of the pump chamber and pump the fluid from the pumping chamber.

An outlet or delivery valve is provided for closing the outlet passage to a variable orifice size so that the valve mechanism gradually retracts to permit restricted fluid flow from the pump chamber past the outlet valve when movement of the outlet pumping actuator pressurizes the fluid in the pumping chamber to a predetermined pressure. The outlet valve can be electronically controlled to allow the pressure in the pump chamber to be automatically controlled in a predetermined manner, as by controlling it to a constant pressure level selected by the user. The semi-rigid carrier is provided with an orifice in the concave outlet depression, so that a sensor can measure the fluid pressure in the outlet pump chamber directly through a flexible membrane, such as another flexible sheet, and can detect various conditions, including potentially dangerous conditions such as a lack of fluid, valve failure, and fluid obstructions.

In accordance with another aspect of the present invention, a carrier having concave depressions for both the inlet and outlet pumping chambers further includes concave passage depressions which are than the inlet passage, transfer passage, and outlet passage, as formed between the flexible sheet and the rigid carrier. The concave passage depressions correspond in location to inlet, transfer and outlet valve mechanism, so that alignment of the passages with the closing valve mechanism results in positive closure.

Another feature of the invention is positive sealing in the valve areas of the passages, which results from a specific structure produced by an improved RF welding method. The unique structure results from welding o a single flexible sheet composed of polyvinyl chloride (PVC) to a relatively thicker, rigid carrier composed of a copolyester material. One aspect of the inventive RF welding method provides successful welding at the surface. The method includes preheating RF die heads, so that a die head contacting the thin PVC sheet is at a higher temperature than another die head contacting the PVC sheet, adjusted so that the RF weld point occurs at the interface between the PVC sheet and the copolyester carrier.

Another aspect of an inventive RF welding method eliminates the adverse consequences of weld extrusion into the transfer valve passage and into the restriction valve passage.

BRIEF DESCRIPTION OF THE DRAWINGS

A more complete understanding of the invention may be had by reference to the following detailed description and claims when taken in conjunction with the accompanying drawings, wherein like elements are represented by like numerals and wherein:

FIGS. 5, 6, and 7 illustrate schematically the operational sequence of an infusion pump according to one embodiment of the present invention;

FIG. 8 is a schematic diagram of a microprocessor control circuit;

FIG. 9 is a schematic process flow diagram of the method of construction according to the present invention;

FIG. 11 is a side cross-sectional view taken along line 15—15 of the cassette assembly of FIG. 2;

FIG. 12 is a schematic assembly view of an alternative embodiment of a coupling mechanism according to the present invention;

DETAILED DESCRIPTION OF THE PREFERRED EMBODIMENTS

Figure 1:
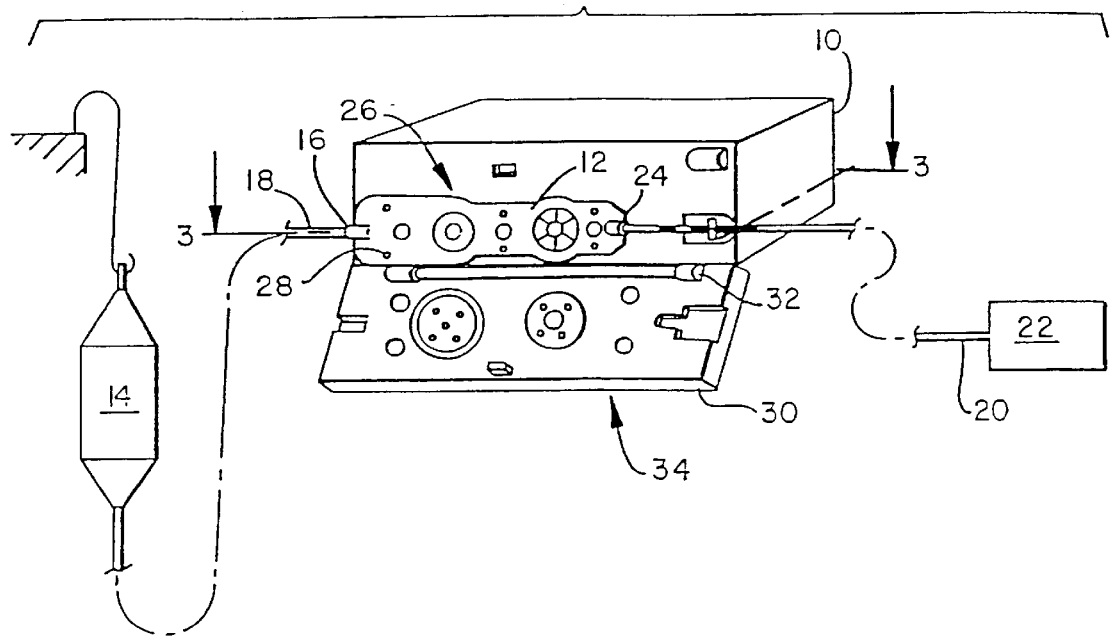
FIG. 1 is a schematic representation of an infusion pump forming one embodiment of the present invention.

As illustrated in FIG. 1, the pumping system is composed of a pumping instrument 10 in which a disposable cassette 12 is mounted for operation. The supply container 14 containing the fluid to be infused may be positioned above or below the cassette 12 and is connected to inlet 16 of cassette 12 by means of tubing 18. Outlet tubing 20 extends to the patient 22 from the outlet 24 of cassette 12.

At the front of the instrument body 10 is a cassette receiving and actuating section 26, including cassette positioning pins 28. A closable door 30 is pivotable about hinges 32 for replaceably holding the cassette 12 within the cassette receiving section 26 properly aligned as with alignment pins 28 for operational confrontation between the cassette and the pumping instrument. A data display/operator input panel 34 may be formed on the front of instrument body 10 and preferably is formed on the front of closable door 30 for display of operational data and for operator input while the cassette is held in place by closure of door 30. The details of the actuator receiver section will be more fully explained below with reference to FIGS. 3 and 4.

Figure 2:
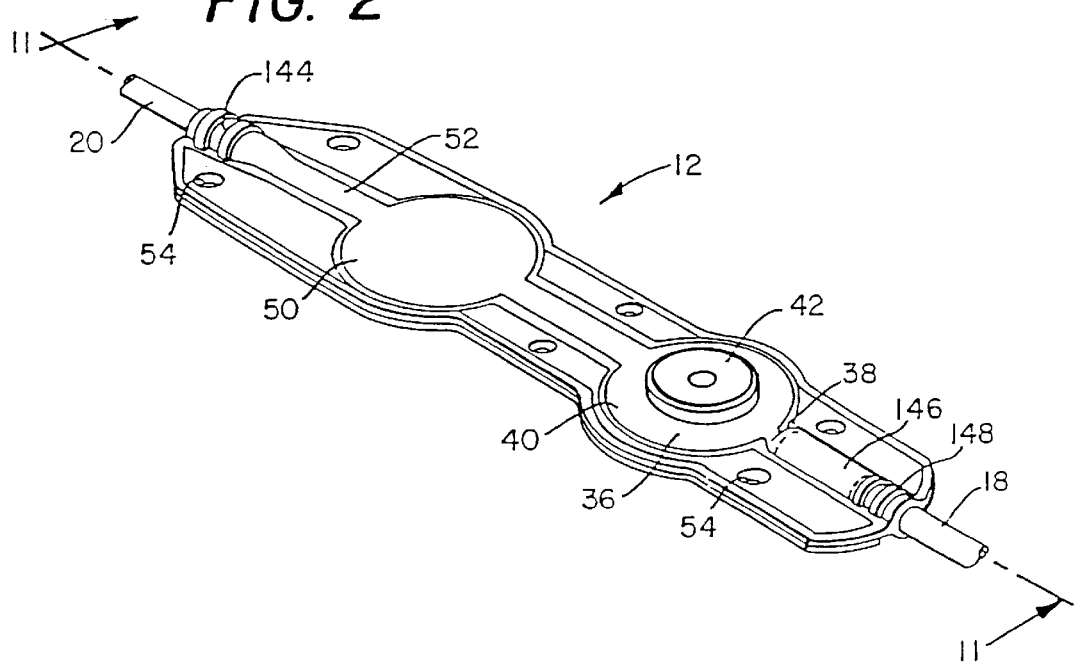
FIG. 2 is a perspective view of a disposable cassette according to one embodiment of the present invention.

A preferred embodiment of the disposable cassette assembly 12 is shown in a top plan view in FIG. 2. The cassette has an inlet chamber 36 which is in fluid communication with inlet 16 through inlet passage 38. One wall 40 of inlet chamber 36 is flexible, and forms a flexible wall 40 having affixed thereto a portion 42 of a detachable coupling mechanism 44.

In the embodiment of the disposable cassette 12, shown in a perspective view in FIG. 2, the portion 42 of the coupling mechanism 44 is a magnetically attractable disk, such as a metal disk which is affixed to flexible wall 40. As will be more fully understood with reference to FIG. 3, disk 42 couples with magnet 46 which is attached to inlet pumping actuator 62 and forms the second portion of detachable coupling mechanism 44. Fluid is received into inlet chamber 36 through inlet passage 38 and is transferred out of inlet chamber 36 through transfer passage 48 and outward from the cassette through outlet 24.

Preferably, the cassette 12 also defines an outlet pumping chamber 50 which receives fluid through transfer passage 48 and from which fluid is pumped through outlet passage 52 to outlet 24 and is delivered by tube 20 to the patient 22. As will be more fully explained below in connection with the construction of the cassette assembly 12 as set forth in FIGS. 9 through 11, alignment holes 54 are formed for alignment during the construction of the cassette assembly and also for alignment during installation of the cassette assembly within the cassette receiving and actuation section 26 of the pumping instrument 10.

Figure 3:
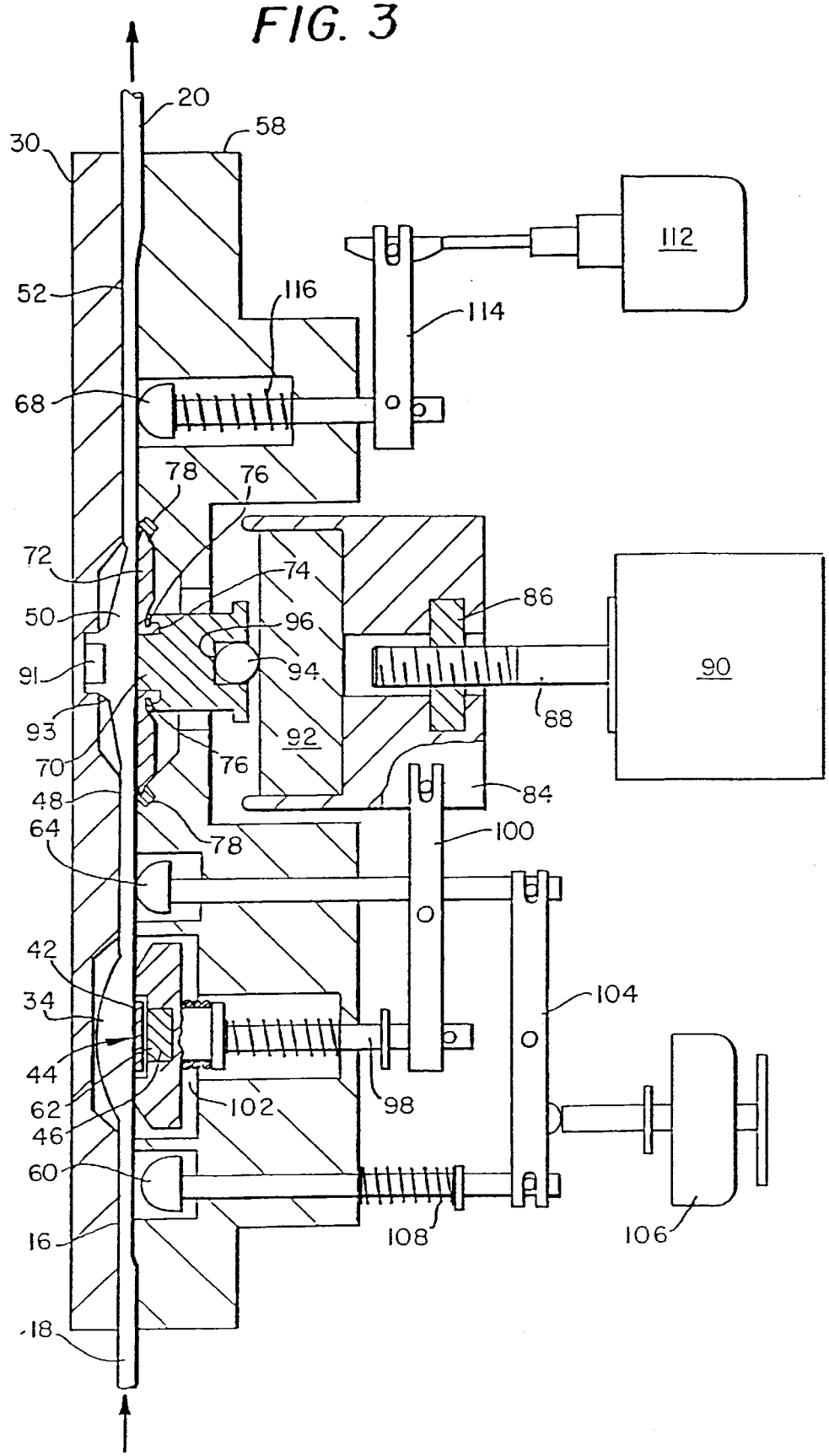
FIG. 3 is a cross-sectional view of the infusion pump of FIG. 1 taken along a horizontal plane through a center line of an installed disposable cassette.
Figure 4:
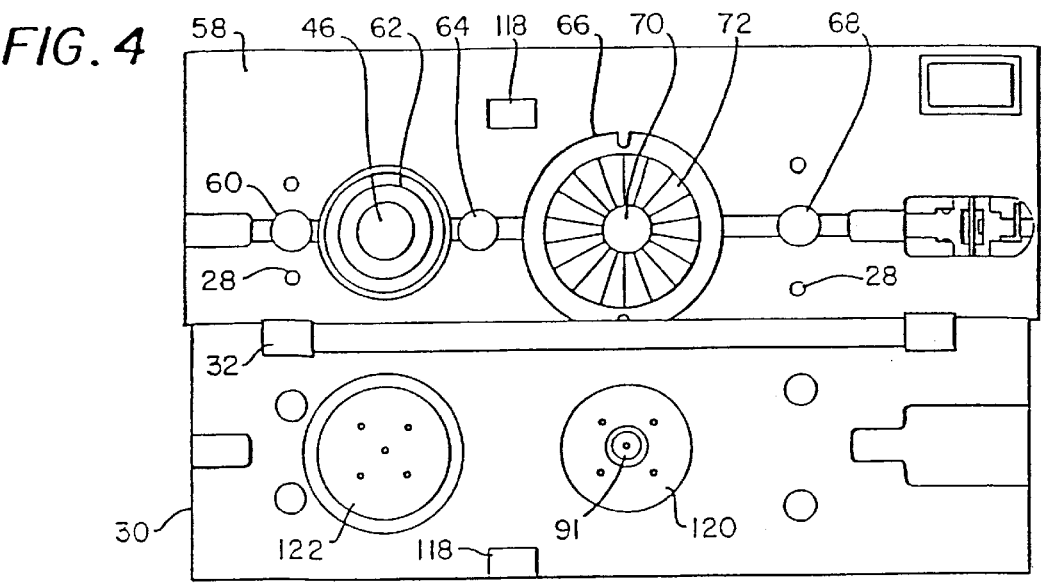
FIG. 4 is a schematic front view of the pump prior to insertion of the disposable cassette according to the present invention.

The details of construction of the cassette receiver actuator section 26 are best illustrated in FIGS. 3 and 4. FIG. 3 is a cross-sectional view of pumping, body 10 taken along a horizontal plane through the pumping instrument and disposable cassette. FIG. 4 is a front view of the cassette receiving section 26 of the pump 10 prior to mounting the disposable cassette 12. The moving members which confront and act upon cassette 12 when it is in an operating position are arrayed on panel 58 secured to the instrument body 10. Proceeding from upstream, the major elements are inlet valve 60, inlet actuator 62, transfer valve 64, outlet pumping member 66, and outlet valve 68.

The outlet pumping assembly 66 preferably includes a central hub 70 surrounded by a plurality of petal-shaped sections 72 to form the movable pressing surface which produces pumping pressure in the outlet pumping chamber of the disposable cassette 12. The hub 70 may be formed by press fit of a male hub member and a female hub member. A circular recess 74 near the outer edge of hub 70 is formed between the male and female hub members. Each petal section 72 is provided on the rear face of its inner end with a smooth hook-shaped curve portion 76 which corresponds to a smooth curve provided on the hub recess 74. The inner edge of each petal section 72 is pivotally retained in the hub recess 74, with the complementary smooth curves of each member permitting relative pivotal movement of each petal-shaped section with respect to the hub about an axis perpendicular to recess 74. The instrument body panel 58 is provided with an annular recess that circumferentially surrounds petal nest 78, which retains the outer end of each petal-shaped section 72. The confronting surfaces of petal nest 78 and the outer end of each petal-shaped section 72 are also shaped for smooth pivoting of the petal-shaped sections with respect to the instrument body. A movable carriage 84 is mounted behind hub 70 and carries a drive nut 86 which is engaged with the threads of a threaded motor shaft 88 rotated by stepper motor 90. The forward end of carriage 84 may be recessed to receive a load cell 82 which has its central force measuring diaphragm confronting a metal ball 94 retained in a rear central recess 96 formed on hub 70. Preferably, however, a pressure sensor 91 is positioned and carried in door 30 for direct contact against the second wall 93 of the outlet pumping chamber 50 of cassette 12. The pressure sensor 91 will have improved pressure reading accuracy over a load cell 82 because of its substantially direct access to pressure chamber 50 without sensing frictional variations due to variable sliding conditions of pumping actuator 70 and associated movement of petals 72. Also, a more direct pump actuation may be accomplished with the door-mounted pressure sensor 91, as the load cell 82 and associated metal ball 94 may be replaced with a continuous connector shaft 95 as schematically depicted in FIGS. 5 through 7, from stepper motor 90.

Rotation of stepper motor 90 acts through the cooperation of threaded motor shaft 88 and the carriage nut 86 to drive carriage 84 forward. This action transmits force to hub 70 moving the hub forward. The translational motion of hub 70 also causes each petal-shaped section 72 to pivot near each of its ends. The petal assembly thus forms a truncated cone of varying height-as the hub moves between the extreme retracted position and advanced position, as depicted in FIGS. 5 and 6.

Inlet actuator 62 is carried forward by refill shaft 98 which is either advanced forwardly or retracted rearwardly through lever 100 acted upon by carriage 84. Thus, as viewed in FIG. 3, when carriage 84 is moving forwardly to push the outlet pump assembly 66 forward, the action of refill lever 100 causes shaft 98 and inlet pump member 62 to be withdrawn, withdrawing metal disk 42 and inlet pump chamber diaphragm 40 with it. As motor 90 is driven in the opposite direction to withdraw carriage 84, lever 100 allows the inlet pumping member 62 to move forward. Spring 102 biases member 62 to its forward position and thus carriage 84 to the rearward direction.

Inlet valve 60 and transfer valve 64 have rounded surfaces for engaging the flow path of the cassette 12 and are operated in tandem fashion through inlet valve lever 104 driven by solenoid 106. When one of the two valves is in the open or rearward position, the other is necessarily in the closed or forward position. Preferably, the parts are assembled so that in the middle of the path of travel of valve lever 104, both valves 60 and 64 are closed to insure no bypassing of fluid. Bias to inlet valve lever 104 is provided by spring 108 surrounding the inlet valve shaft, which biases the arrangement to the condition of inlet valve 60 open, transfer valve 64 closed.

Outlet valve 68 is operated by a stepper motor 112 acting upon delivery lever 114 and is biased to the closed position by spring 116. The linear stepper motor 112 is capable of positioning the delivery restriction valve 68 in any selected position from fully retracted or open position as shown, to a fully extended or closed position. This permits the output from outlet pumping chamber to be metered according to the selected opening position of the delivery restriction valve 68.

As indicated previously, actuator panel 58 is provided with mounting pins 28 corresponding to the alignment in mounting holes 54 in cassette 12. The actuator door 30 is mounted to panel 58 by hinges 32 and is closed by latch 118. As a double check for patient safety, opening of door 30 will stop pumping and sound an alarm. In the inner face 110 of door 30, concave depression 120 is arranged to confront petal assembly 66 when the door is closed, and similar concave depression 122 confronts the refill actuator 62. Depressions 120 and 122 may be provided with air vent holes through the front door to facilitate closing the door with cassette 12 in position. With the cassette mounted on pins 28, the inlet fluid chamber 36 and the outlet pump chamber 50 are captured between the inlet actuator 62 and outlet member 66 and the depressions 122 and 120, respectively. In the operating position, valve 60 is adjacent inlet passage 38 to close off the inlet when the valve member 60 is extended. Likewise, valve 64 may be activated to close off transfer passage 48.

The delivery valve 68 may be activated to selectively close outlet passage 52 to an orifice of any desired size. The pumping compartment defined between the rigid wall of depression 120 and the outlet pump petal assembly 66 is filled by the fluid from an inlet chamber 36 when the petal assembly 66 is in its retracted position, and the outlet pump chamber 50 is bulged with fluid at a low fluid pressure of approximately ten (10) inches of water. The volumetricity of pumping is then provided by the accuracy of volume displaced between the extreme positions of outlet pump assembly 66 and the compliance of the exterior wall of outlet pump chamber 50 to the moving truncated cone surface presented by petal pump assembly 66.

As will be discussed more fully below, the material used to construct the cassette is flexible, and therefore conforms to the surface of the petal elements so that the position of the petal assembly defines the volume of fluid enclosed between it and the rigid surface on the other side very precisely. The volumetric performance of this arrangement is defined almost completely by the movement of the hub 70 and thus, the petal-shaped sections 72 and not by the mechanical properties of the disposable cassette element which is confined from movement. The volume displaced by the petal assembly varies in a linear fashion with translational movement of hub 70.

As illustrated in FIG. 8, the system is operated under the control of a microprocessor system 124. The microprocessor controls the movement of solenoid 106 between two positions: (1) inlet valve open, transfer valve closed, and (2) inlet valve closed, transfer valve open. Likewise, microprocessor 124 controls delivery valve stepper motor 112 to select the total or partial restriction imposed by delivery valve 68 on the cassette outlet passage 52. Microprocessor 124 also selects, in accordance with the rate selected by the operator on input panel 34, the rate of movement of the pumping stepper motor 90. Continuous control over operation, diagnostics and aberrant conditions are principally provided by either a load cell 82, which measures the force being exerted on pumping assembly 66, or by pressure sensor 91 which directly measures the pressure in the outlet pump chamber 50, as exerted by petal assembly 66. As indicated previously, a door-mounted load cell 91 is preferred for accurate pressure measurement. This data is continuously provided to microprocessor 124 or through analog to digital converter 126.

A typical cycle of operation is illustrated in FIGS. 5 through 7. FIG. 5 illustrates the condition of the actuator and disposable cassette as the delivery portion of the cycle has begun. At this stage, the outlet pump chamber 50 has been completely filled with fluid to occupy the compartment formed between the cassette outlet chamber depression and the fully retracted petal assembly 66. Delivery valve 68 and transfer valve 64 are closed, completely capturing the fluid in outlet pump chamber 50. Inlet valve 60 is opened while the transfer valve 64 is closed, so that fluid may be drawn into the inlet fluid chamber 36 as inlet actuator 62 is retracted. The microprocessor begins the initial stage of the delivery cycle by directing the outlet pump stepper motor 90 to advance to begin pressurization of fluid in outlet pump chamber 50. During the first few steps of stepper motor operation, valves 68 and 64 remain closed to permit this initial pressurization. Elevation of the pressure caused by the advancement of petal assembly 66 is sensed by pressure sensor 91 which data is fed to microprocessor 124. This serves as a diagnostic step to verify the capturing of a full load of fluid in the outlet pump chamber 50. A failure to pressurize in the first several steps of motor 90 indicates a system problem. It could be that the fluid supply is depleted, so that the outlet pump chamber 50 has not been filled, or that the inlet actuator mechanism has not appropriately filled inlet supply chamber 36. Another possibility is that a defect in valve 64 or 68 is permitting fluid to leak from chamber 50. In any of these events, operation of the instrument will be stopped by the microprocessor 124 and an alarm sounded.

If, however, normal pressurization occurs, microprocessor 124 instructs delivery valve 68 to open as motor 90 advances, to deliver fluid to the patient through outlet 20, as illustrated in FIG. 6. Continuous monitoring of the pressure sensor 91 permits the microprocessor to exercise continuous control over delivery valve 68 to selectively restrict the outlet passage 52. This permits the device to insure that the delivery rate is not higher than the requested rate, as for example, where gravity siphoning occurs. The microprocessor is also programmed with a selected maximum pressure limit, set by the user through display/input panel 34, which is used in continuous pressure monitoring. Escalation of pressure above the selected maximum pressure even with the delivery valve 6S wide open, will result in alarm and shut-down of the instrument, indicating that there is some condition which requires attention, and that fluid is not reaching the patient. The ability to select a maximum pressure limit by the user permits relatively rapid alarms, even at relatively low selected infusion rates.

Preferably, the microprocessor is programmed to maintain a relatively constant pressure in outlet pump chamber 50 by selected restriction of delivery valve 68, such constant pressure being just below the maximum pumping pressure selected by the operator. This is helpful in insuring that there are no variations in volumetric delivery which might result from operation at varying pumping pressures.

While fluid is being delivered by advancement of petal assembly 66, the inlet actuator 62 is automatically being withdrawn, transfer valve 64 is already closed, pulling with it flexible wall 40 through coupling 44, and fluid is drawn by negative pressure into the inlet chamber 36 through open inlet passage 38. When the outlet pumping assembly 66 has reached its full extended position, inlet and outlet valves 60 and 68 close and transfer valve 64 opens. Microprocessor 124 then reverses stepper motor 80 for rapid retraction of petal assembly 66 and a rapid extension of inlet actuator 62 as illustrated in FIG. 7. This permits a very quick transfer of fluid into outlet pump chamber 50 which will arm the device for the next delivery cycle. During the outlet pumping portion of the delivery cycle, energy was stored in spring 102 immediately behind the inlet pumping member 62. This energy is used to effect the transfer of fluid so as to drastically reduce the mechanical loading on the main pump motor. The purpose of this is to allow an increased motor speed during the fluid transfer step which in turn reduces the time taken to effect the transfer as it is principally limited only by the maximum operating speed of the main outlet pump motor 90. Once the transfer of fluid is complete, valve 60 opens and valve 64 closes, and the system is in a condition once more indicated in FIG. 5. A mechanical stop on shaft 98 limits the amount of movement of the inlet refill actuator 61 so as to avoid pumping any fluid back towards the fluid container 14 as valve 60 opens. Accuracy of the pump is facilitated by having the ability to completely seal the passages, and particularly the transfer passage and the outlet passage. Thus, the outlet chamber can be pressurized under controlled, non-leaking conditions. A desired pressure can be carefully maintained during delivery by partially opening the outlet valve, which acts as a restriction valve. The fluid delivery can then be completely and accurately controlled.

Figure 10:
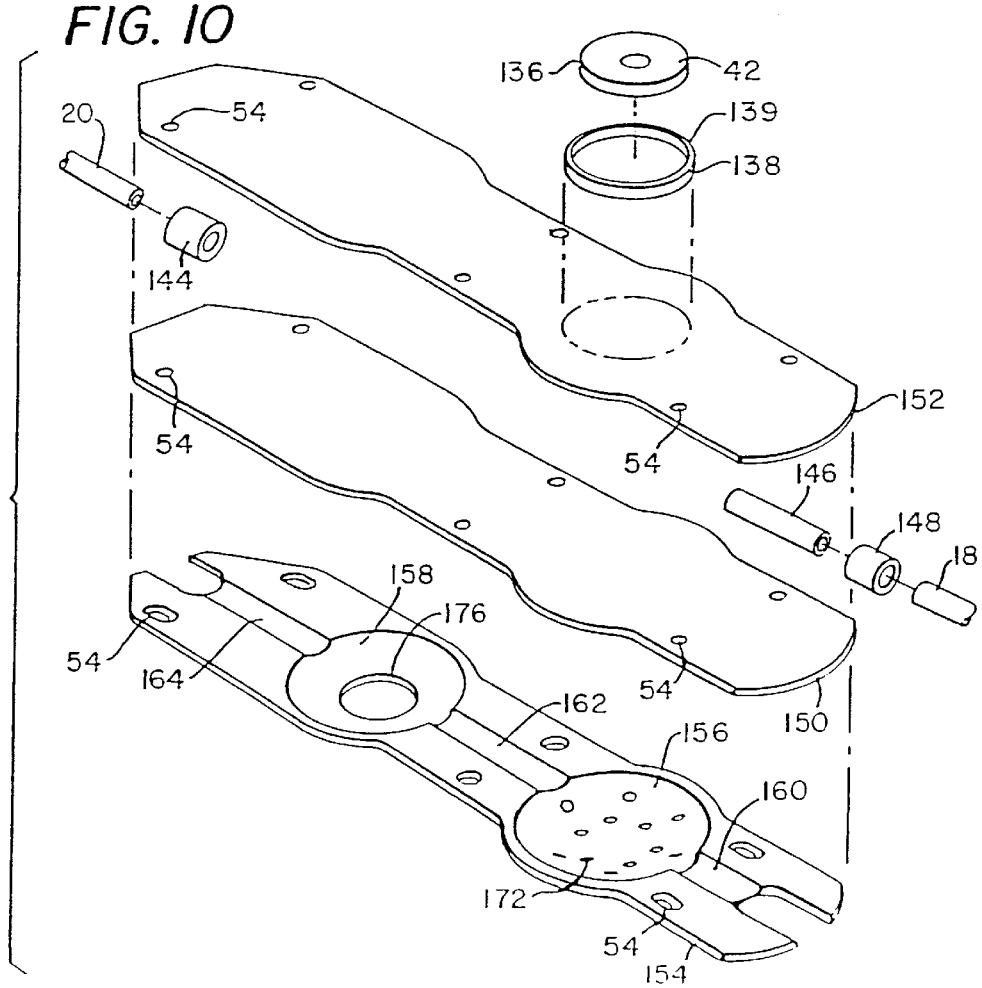
FIG. 10 is a perspective view schematically depicting the assembly construction of the cassette according to the present invention.

With reference to FIG. 9, in conjunction with FIGS. 10 through 11, the construction and construction process of one preferred embodiment of a disposable cassette assembly according to the present invention will be more fully understood.

The construction materials, which generally include thin sheet of plastic film, molded plastic carrier plates or moldable plastic for forming plastic carriers, magnetically attractable disks or sheet metal for forming disks, tubing, and an adhesive, are received, as schematically represented by numeral 130. The receiving step may include staging for inspection and quality control 130a, inspecting 130b, and moving the received material to a storage area 130c. The flexible portion of the cassette comprises two sheets 150 and 152 of flexible film such as PVC sheets or one sheet 182 and a pressure transducer membrane 184, which are cut or blanked at step 132 to an appropriate length and shape corresponding to the pump receiving and holding section.

Typically, the flexible PVC film is received in rolls which are de-reeled, placed under pressure, punched or cut to an appropriate shape, and placed in a container for use in the next step. A portion 42 of the coupling mechanism 44 is then welded to a second sheet 152 of the film or to a single sheet 182 at step 134. In the preferred embodiment, a flat metallic disk 42 is formed in a flat circular shape having a perimeter ledge 136 therearound. Disk 42 is welded to a shallow plastic tray 138, as shown in FIG. 10. Preferably, plastic tray 138 has a rim 139 which surrounds and overlaps ledge 136 as it is attached to the disk 42 as by ultrasonic welding, or as by an injection molding process to encapsulate disk 42 within plastic tray 138. Disk 42 with the plastic tray affixed thereto is positioned on the second film strip and welded to the film strip in step 140.

Other detachable coupling mechanisms could be similarly welded in step 140. For example, a mechanical clip 44a is depicted in FIG. 12 which connects to a pair of clip receptors 42a and 46b which are attached to the cassette and the inlet actuator, respectively. Such an alternative clip could be advantageous for purposes of specialized Nuclear Magnetic Resonance (NMR) or Magnetic Resonance Imaging (MRI) fluid infusion. However, the simplicity of the magnetic coupling is normally preferred.

At step 142, tubing is cut. An appropriate length of outlet tubing 20 is cut. An outlet connector plug 144, which is a larger diameter tube and which receives outlet tube 20 is cut. A short section of flexible support tubing 146 is cut for insertion into inlet passage 38. An inlet plug connector tubing 148 is cut and an appropriate length of supply tube 18 is cut. The outlet tubing 20 is inserted into the outlet connector plug 144; the flexible support tube 146 is inserted partially into the inlet connector plug; and, the supply tube 18 is partially inserted into the opposite end of the inlet connector plug.

As shown in FIG. 10, the inlet and outlet tubing assemblies are placed in alignment between the first sheet 150 and the second flexible sheet 152 to which the metal disk has been welded. The sheets 150 and 152 are sandwiched about the aligned tubing and welded together to thereby sealingly connect each of the flexible sheets to the outlet connector plug and the inlet connector plug and to define a sealed fluid path through the cassette, including an inlet passage 38, an inlet pumping chamber 36, a transfer passage, an outlet pumping chamber, and an outlet passage. The inlet passage has a portion thereof immediately adjacent the inlet chamber which is narrower than the remainder of the inlet passage to thereby hold the inserted flexible support tube 146 within the inlet passage without permitting it to slide into the inlet chamber. The flexible support tube 146 has sufficient resiliency to advantageously prevent collapse of the inlet passage 38 due to the negative pressure caused during the drawing back of the flexible wall 40 of the inlet chamber 36. Fluid from supply tube 18 freely flows into the inlet chamber 36 without being restricted by a collapsed inlet passage 38. The support tube 146 is sufficiently flexible to permit complete closure by inlet valve 60, although it has been found that small amounts of leakage at the inlet valve are not critical because of the rapid rate of the transfer from the inlet chamber 36 to the outlet pumping chamber 50.

With reference to both FIGS. 10 and 11, one preferred embodiment of a carrier plate 154 is formed having concave indentations 156 and 158 for receiving the inlet chamber and outlet pumping chamber. The carrier plate is rigid, relative to the flexible sheets 150 and 152, and may be composed of a plastic, such as PVC (but preferably a copolyester), which has a thickness several times greater than that of the flexible sheets. Also formed in the carrier plate 154 are indented troughs or channels 160, 162, and 164 corresponding in location to the inlet, transfer and outlet passages. The troughs or channels are shallow, having a radius of curvature 165 corresponding to that of the valves 60, 62, and 64 and are substantially wider than the width of the passages 38, 48 and 52, which are formed between the first and second sheets 150 and 152. This facilitates complete sealing, because the valve head matches the channel size and radius, so that the narrower passages are completely compressed and closed by the valve head and channel. The welded flexible sheet portion is aligned through locating holes 54 and corresponding locating holes 54a on the carrier plate 154. Thus, the extra width of the channels will give additional tolerance in the alignment with the passages, which facilitates manufacture without adversely affecting the functionality of the cassette.

The construction method as in FIG. 9 of the disposable cassette assembly as shown in FIG. 10 includes a step 166 of welding the flexible portion of the cassette to the rigid carrier. Prior to welding, an adhesive material 168, such as one which can be cured by ultraviolet (UV) radiation, is applied at step 170 to the inlet chamber concave depression 156. The layered flexible assembly is located and welded in place at step 166. Subsequently, a negative pressure is applied through vent holes 172 to the depression 156 to draw the second flexible layer 152 against the concave depression 156. Ultraviolet radiation is applied at step 174 to cure the adhesive while it is drawn firmly against the depression wall. Alternatively, a positive pressure could be applied to the opposite side of the flexible sheets adjacent the depression, either internal to the two flexible sheets or externally to the first flexible sheet to which the metallic disk is welded. The negative pressure is preferred as it avoids potential contamination by pressurization inside the cassette and also avoids potential uneven pressure due to pressing through the magnetic disk.

The outlet pumping chamber cavity has an orifice 176 formed therein through which the door mounted pressure load cell 91 may sense the pumping pressure directly through the second thin flexible sheet 152 of cassette 12.

It will be appreciated that the cassette and instrument could be designed without separate input and output pumping chambers, and that a single pumping chamber activatable both for drawing supply fluid in from a negative head pressure, and pumping the fluid positively to the patient through a metered control valve could be constructed, without departing from certain aspects of the present invention. However, it is believed that improved reliability, improved diagnostic monitoring, and improved control are advantageously achieved using an input pumping chamber to draw fluid from a supply without regard to positive or negative head height of the supply, in combination with a separate outlet pumping chamber which can be carefully monitored directly through the exterior flexible wall thereof to accurately monitor and apply pressure to the patient.

While the foregoing alternative embodiment has been described primarily with respect to a double-sheet construction in which one of the flexible sheets is attached to a rigid carrier and thereby rigidified, it has been found that other advantages may be obtained through reduced cost, both in the materials used and in the processing steps required through the construction of an embodiment of the disposable cassette in which a single flexible sheet of PVC film is welded to a rigid carrier formed of a thicker injection-molded plastic, preferably a copolyester plastic. Also, as will be more fully understood from the description below, additional advantages have been obtained with unique, improved manufacturing methods—particularly, improved RF welding of thin sheets of PVC to relatively thicker, rigid carrier composed of copolyester. The resulting structure produces a fluid-tight flow path between the single flexible sheet and the rigid carrier. The flow path includes an inlet passage, an inlet pumping chamber (i.e., suction pump chamber), a transfer passage, an outlet pumping chamber and an outlet passage.

As noted previously, one key aspect for maintaining accurate fluid delivery from a cassette, which may be used in a pump for drawing fluids from a negative head height, is in the capability of a cassette transfer valve and an outlet valve (or delivery valve) to completely and reliably shut off all fluid flow. The outlet pumping chamber, or delivery pumping chamber, can be made completely fluid-tight through valve operation. Leakage back from the outlet pumping chamber to the inlet pumping chamber is eliminated, and any delivery of fluid through the outlet valve can also be precisely controlled without any unwanted flow or with precisely controlled restricted flow. This capability must also be provided in conjunction with weld seams capable of holding both positive and negative fluid pressures of 15 psi or more exerted over the entire surface area of the fluid flow pathway, both in the inlet, transfer and outlet channels and also in the inlet and outlet pumping chambers.

Figure 13:
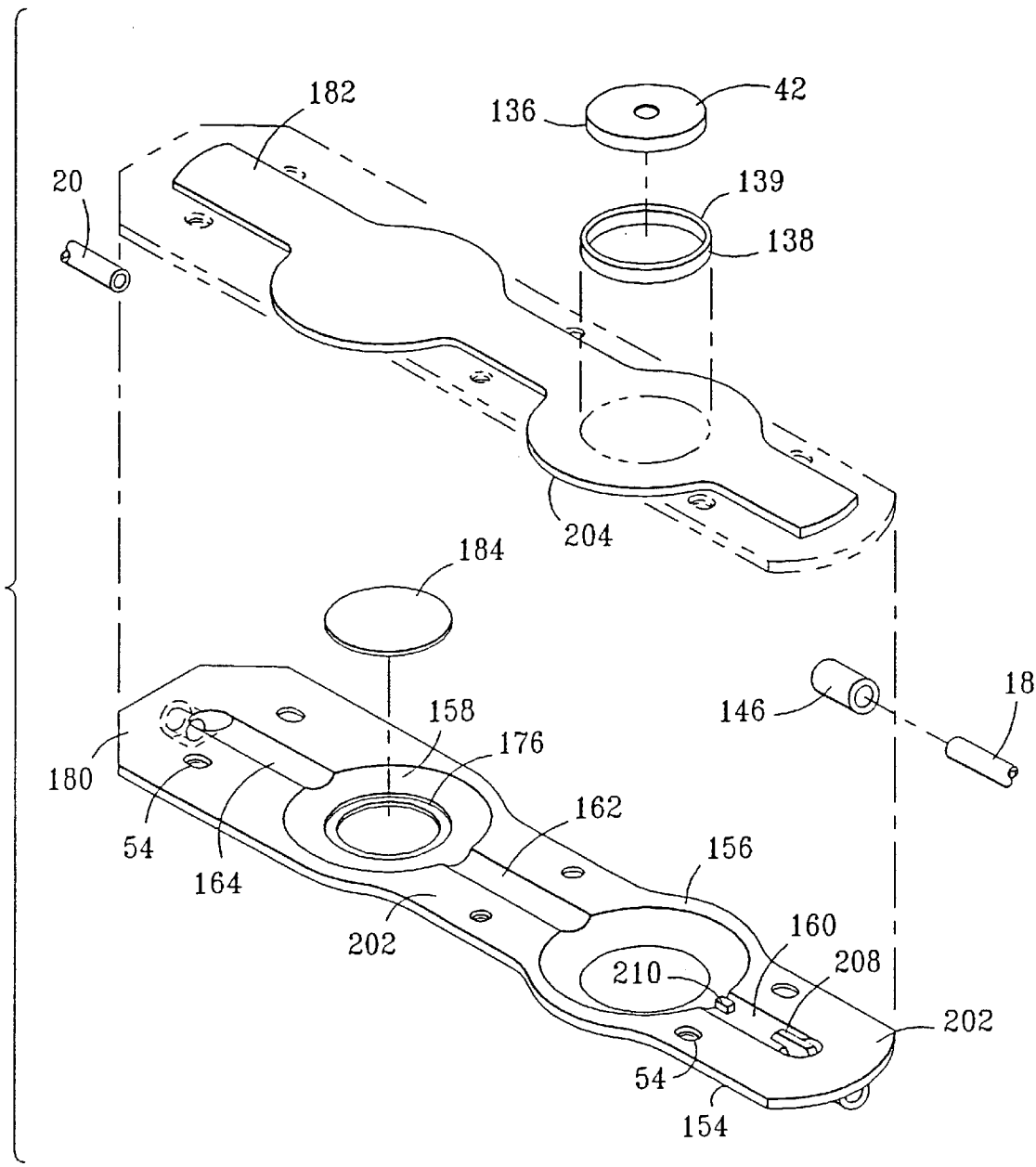
FIG. 13 is a perspective assembly view of an embodiment of the cassette formed with one sheet of flexible PVC to be welded directly to a rigid carrier to form a fluid passage therebetween.
Figure 14:
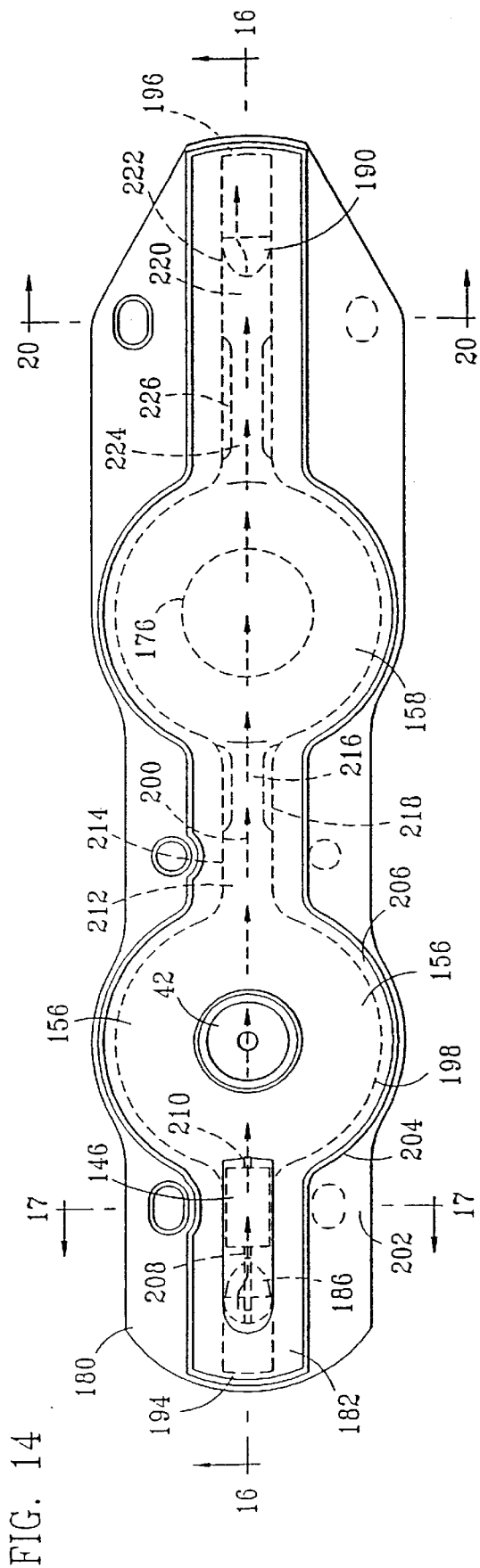
FIG. 14 is a top view of a single sheet cassette, according to one embodiment of the present invention.
Figure 15:
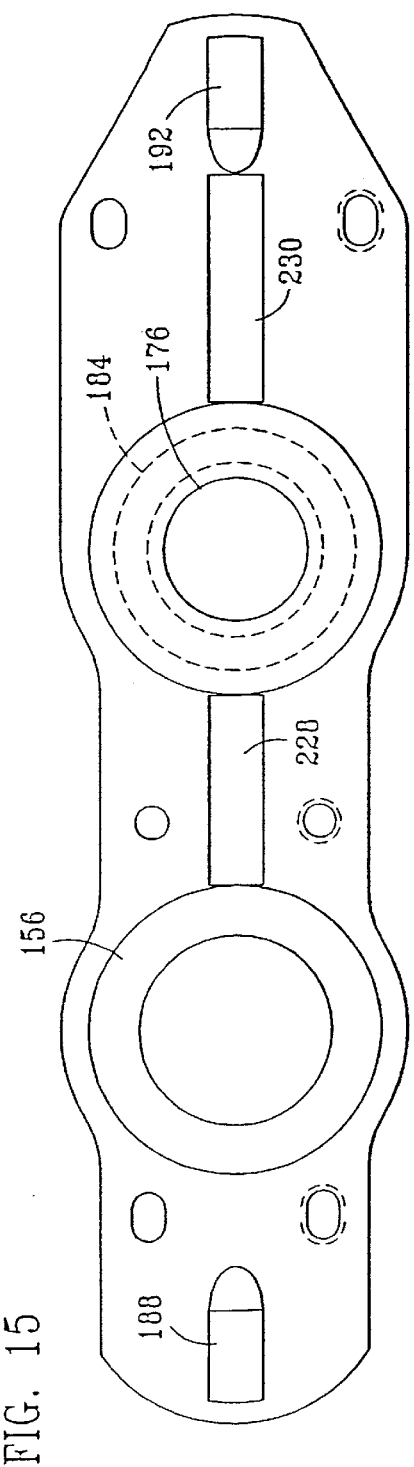
FIG. 15 is a bottom view of the cassette of FIG. 14.
Figure 16:
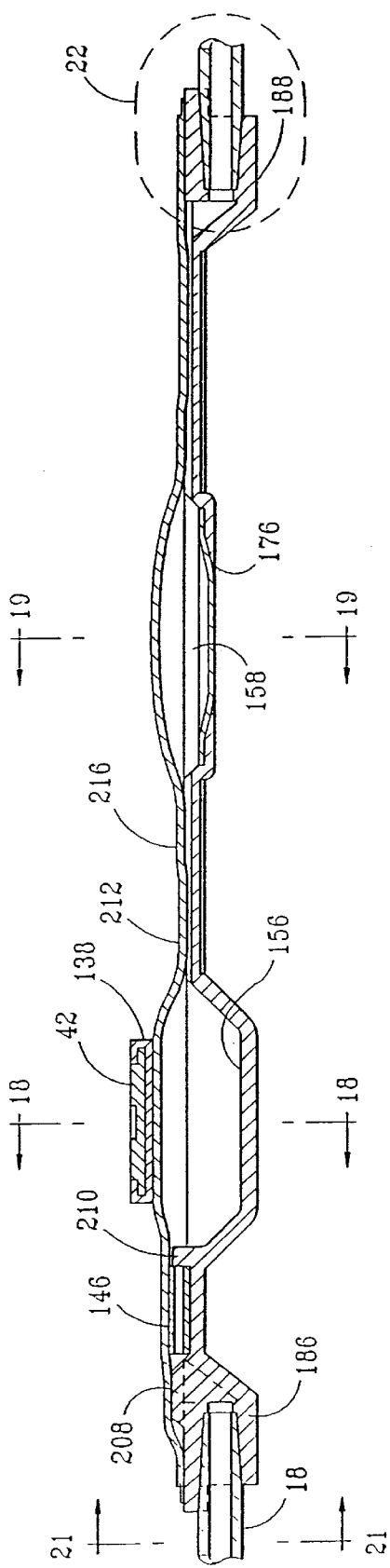
FIG. 16 is a central cross-sectional view taken along a centerline 1616 of FIG. 14.
Figure 22:
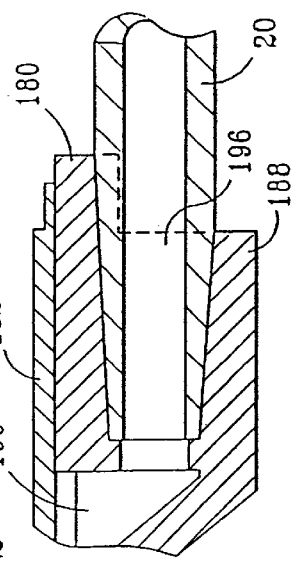
FIG. 22 is an enlarged partial detail cross-sectional view of the inlet boss and orifice at 22 of FIG. 16.
Figure 21:
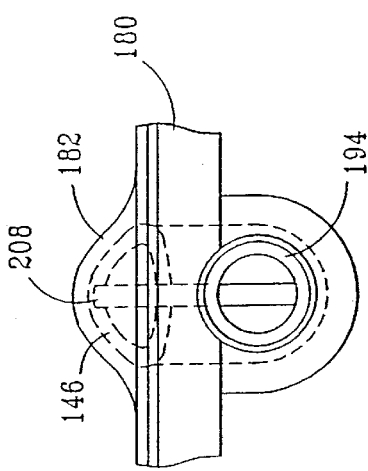
FIG. 21 is a cross-section at 21—21 of FIG. 16.
Figure 17:
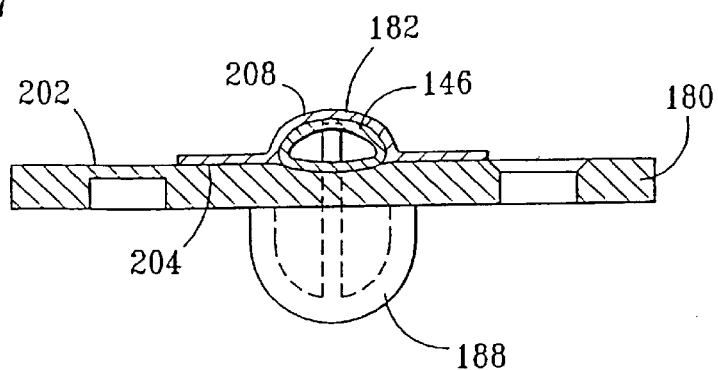
FIG. 17 is a cross-section at 17—17 of FIG. 14.
Figure 18:
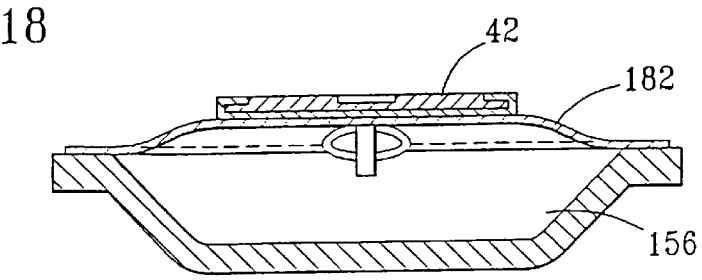
FIG. 18 is a cross-section at 18—18 of FIG. 14.
Figure 19:
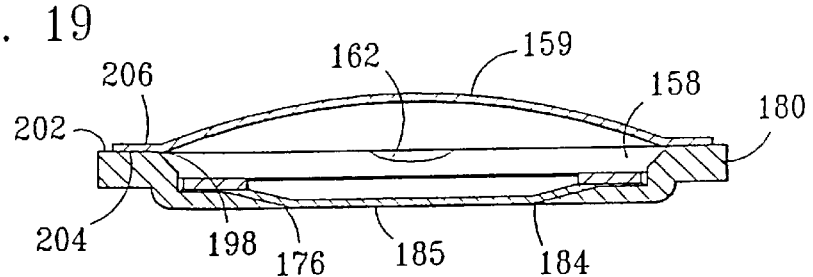
FIG. 19 is a cross-section at 19—19 of FIG. 16.
Figure 20:
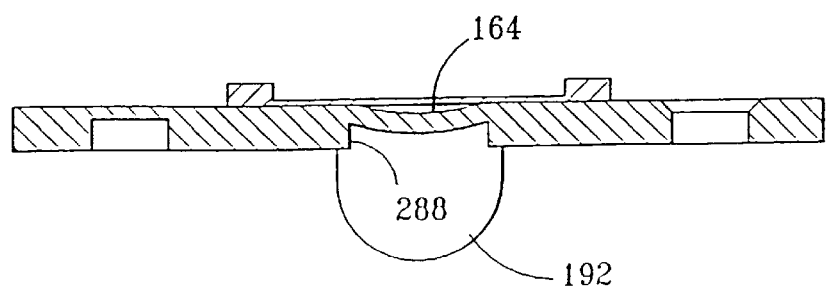
FIG. 20 is a cross-section at 20—20 of FIG. 16.

The unique structure and construction of a preferred embodiment, having a single flexible layer 182 welded to a rigid carrier 180, will be more fully understood with reference to FIGS. 13 through 22, below. FIG. 13 is a perspective assembly view of this alternative preferred embodiment of a disposable cassette. FIG. 14 is a top plan view of the assembled cassette of FIG. 13. FIG. 15 is a bottom plan view of the assembled cassette. FIG. 16 is a side section view, taken along a center line of the cassette of FIGS. 13–15, according to the present invention. FIG. 17 is a cross-sectional view, taken along section lines 17—17 of FIG. 14. FIGS. 18 and 19 are cross-sectional views, taken along section lines 18—18 and 19—19, respectively, of FIG. 16. FIG. 20 is a sectional view, taken along section line 20—20 of FIG. 14. FIG. 21 is a partial end view from the inlet end of the inlet boss 186 of the inventive cassette, according to the alternative construction, using a single flexible sheet 182. FIG. 22 is a partial enlarged, cross-sectional detail of the outlet boss 188 and tapered hole tube connector 196 formed therein.

Referring now to FIGS. 13 and 14, one preferred embodiment of a disposable cassette includes a rigid carrier plate 180, formed as with injection molding, having a first concave indentation 156 for forming the inlet pumping chamber and a second concave indentation 158 for forming the outlet pumping chamber. The carrier plate 180 is preferably composed of a copolyester plastic material, such as Eastman Extar DN001, and has a sufficient thickness, so that it is rigid relative to the thin, flexible PVC sheet 182. The single sheet 182 is preferably composed of another, more flexible plastic, such as medical grade PVC. PVC sheets available from Ellay, Inc., under the designation 30-2127, have been found to meet the requirements of this invention. The thickness of the carrier plate 180 is generally several times thicker than that of the flexible sheet 182, as for example, a flexible PVC sheet 182 having a thickness of about 0.016" (i.e., about 1.6 mil) provides good flexibility and strength, and the rigid carrier 180 having a thickness of about 0.080" (i.e., about 8.0 mil) provides strength, rigidity and dimensional stability for the purposes of the present invention.

The flexible sheet is welded to the rigid carrier, using a radio frequency welding technique. The dies are made of brass or other radio frequency conducting material having appropriate cavities and channels formed therein, corresponding to the concave indentations for the inlet pumping chamber and the outlet pumping chamber, as well as indentations for the channels, including the inlet channel, the transfer channel and the outlet channel, which define the fluid flow path 200 through the cassette. The thin PVC film 182 is preferably held in position to the upper die through the use of a vacuum, which is applied through orifices in the upper die. The rigid carrier 180 is placed in the lower die, appropriately aligned as by using alignment holes 54. The upper and lower dies are pressed together, in alignment with each other, to squeeze together a bottom surface 204 of the flexible sheet 182 and a top flat surface 202 of the rigid carrier 180. An electromagnetic RF signal is communicated through the dies, from one RF conducting die to the other and through the plastic materials "sandwiched" therebetween. Specific inventive aspects of this process will be explained more fully below with respect to FIGS. 23 through 27, below.

In the preferred embodiment, prior to welding the single plastic sheet 182 on the rigid carrier 180, a pressure-sensing orifice 176 will have been formed through the rigid carrier at the outlet pumping chamber 158. Preferably, the orifice 176 is circular in shape and may be formed into the rigid carrier during the injection molding process by which the rigid carrier is formed. A thin plastic membrane 184, which may be composed of the same PVC film materials as the sheet 182, having a thickness of about 0.016" (i.e., about 1.6 mil) is cut, as by a coining process, to a predetermined size and shape for covering the pressure-sensing orifice 176. The coined membrane 184 is secured, covering the orifice 176. Preferably, RF welding is used to secure the membrane 184 in place. Then, the single flexible sheet of PVC is welded to the rigid carrier, as described above.

Also formed in the rigid carrier is a depression 160, corresponding to the inlet channel, which communicates with the inlet pumping chamber 156. There is also an indentation 162, corresponding to the transfer passage between inlet pumping chamber 156 and outlet pumping chamber 158. Extending from outlet pumping chamber 158 is a depression, corresponding to an outlet channel 164. The inlet channel 160 and the outlet channel 164 do not extend entirely across the flat top surface 202 of the carrier 180, but rather communicate through an inlet orifice 186 and an outlet orifice 190. Inlet orifice 186 extends through an inlet boss 188, formed on the bottom surface of the rigid carrier 180. Also, outlet orifice 190 communicates with channel 164 and into an outlet boss 192, formed on the bottom surface of rigid carrier 180. A tapered inlet hole 194 serves for connection of inlet tubing 18 for receiving fluid to be infused, and a tapered outlet hole 196 serves for connection to the outlet tubing 20, which will be used to infuse fluids to a patient. In each instance, the inlet tubing 18 or the outlet tubing 20 will be sealingly secured to the cassette as by adhesive or other bonding method, for example, ultraviolet curing adhesive. Preferably, a solvent bond is used for its speed and low cost, which, together with the tapered construction of the receiving holes, results in mechanically secure and fluid-sealed bonding. For example, Cyclohexanone is one solvent which can be used, as it will partially dissolve both the PVC and the copolyester, which then blend together for effective bonding.

The inlet orifice 186 communicates from the inlet hole 194 and attached tubing into the inlet channel 160, which in turn communicates with the remainder of the flow path 200. The flow path 200 is essentially defined by a perimeter edge 198, between the top flat surface 202 of the rigid carrier and the indentations in the top surface of the rigid carrier, which indentations and perimeter edge 198 define the fluid flow path 200. Fluid flow path 200 is enclosed by welding the thin PVC sheet 182, as with a radio frequency weld formed at the interface between the top surface 202 and the rigid carrier and the bottom surface 204 of the PVC film, which weld 206 extends entirely around the perimeter edge 198, defined by the indentations of the fluid flow path. As with the double flexible sheet embodiment, described above, a metal disk 42 will be attached to the top surface 205 of sheet 182, as described above, with respect to attachment of the disk 42 to the second sheet 152 in the double sheet cassette construction.

Although specific embodiments of the invention have been illustrated in the accompanying drawings and described in the foregoing detailed description, it will be understood that the invention is not limited to the embodiments disclosed, but is capable of numerous rearrangements, modifications, and substitutions of parts and elements without departing from the spirit of the invention. It is intended that the scope of the invention disclosed herein be limited only by the broadest interpretation of the appended claims to which the inventors are legally entitled.

When the disposable cassette is placed in the pumping apparatus, as shown in FIG. 4, inlet channel 160 will be placed adjacent to inlet valve 60. Metallic disk 42 will become removably coupled with magnet 46 for actuation, both in retraction and in compression with inlet pumping actuator 62. As the magnetically-coupled inlet pumping chamber 50 may draw fluid from a negative height, the low pressure within the inlet passage will tend to collapse the flexible sheet 182 into the inlet channel 160. Such a restriction or a closure could interfere with pump operation. In order to prevent this, first and second support projections 208 and 210 are advantageously formed, projecting upward from the bottom of channel 160, a short distance above flat top surface 202. The flexible sheet 182 is supported upward by projections 208 and 210 from either end of the inlet channel 160. The channel area between projections 208 and 210 is not provided with projections, so that valve actuator 60, acting against sheet 182, can overcome the upward tension, thereby closing the inlet passage. It has been found that when valve 60 is actuated to a "closed" position a "clicking" noise can result when a single layer of flexible film 182 is pushed. To reduce the noise level, it has been found advantageous to insert a silicon tubing 146, positioned between projections 208 and 210 and enclosed between channel 160 and PVC layer 182. The silicon tubing 146 is not readily welded with RF welding such that its interposition, between the flexible sheet 182 and the channel 160 of cassette rigid carrier 180, does rot interfere with RF welding of the sheet 182 to rigid carrier 180 and does not require a separate mandrel welding operation to prevent the opening to the center of tubing 146 from becoming sealed shut. It has also been found that, to the extent that a perfect seal around the tubing 146 is not obtained during the welding procedure, the capacity of inlet pumping chamber 156 is, nevertheless, sufficiently larger than the capacity of outlet pumping chamber 158, so that small amounts of leakage at the inlet valve 60 can be tolerated without adversely affecting the operation of the pumping cassette. As discussed above with respect to the double-sheet cassette, and as discussed further below, the accuracy of the pumping cassette is obtained through complete sealing of the transfer channel 162 and the outlet channel 164 on either side of the delivery pumping chamber 158.

To facilitate complete closure of transfer passage 162, upon actuation of transfer valve 64, a unique welding procedure has been implemented, as will be discussed more fully below with respect to FIGS. 23 through 27. It should be noted with respect to FIG. 14 that Applicants' inventive cassette has a first transfer valve area 212, against which valve 64 will impact. At the perimeter edge 198 alongside area 212, there are welds 214 which are specially formed to avoid extrusion of weld material into channel 162. Thus, the valve 62 can seal completely along the radius of the channel 162, from one side of perimeter edge 198 to the other side. At channel 162, there is a second area 216, which is adjacent to the output pumping chamber 158, in which mechanically strengthened welds 218 are provided along both sides of perimeter edge 198. As the transfer area valve area 212 will remain in contact with valve actuator 64, there will be adequate mechanical strength to avoid weld separation, while uniquely providing a smooth weld transition of the channel 162 radius at the perimeter edge 198. The area 216, at which there is no valve contact and at which the maximum pressures associated with controlled pumping in outlet pumping chamber 158, will be securely held with the increased strength welds 218.

As discussed above, in the outlet pumping chamber 158, there is an orifice 176 formed, which has a transducer membrane 184 welded thereover. With reference to FIG. 19, it will be seen that the preferred construction of the pumping chamber includes the orifice 176, having a chamfer edge therearound, with membrane 184 welded thereinto. Thus, a substantially flat transducer surface 185 results across the opening of orifice 176. The weld around the perimeter or membrane 184 can be created with standard RF welding practices, because normal extrusion of material from such a weld, either into the orifice 176 or into chamber 184, does not interfere with the operation of the transducer membrane.

The portion of film 182, which overlays the outlet pumping chamber 158, is provided with an upward radius through the use of concavity in the upper welding die and a vacuum which draws the flexible sheet 182 up into the concave area before welding. The welding then secures the additional "bulge" of sheet 182 in the appropriate radius fashion, so that pumping can be accomplished by the pump actuator 70, as discussed above with respect to the double-sheet cassette.

In the outlet passage 164, there is a valve closure area 220, against which outlet valve 68 will be actuated. The portion of flexible sheet 182, which overlays area 220, is secured to the rigid carrier 180 with unique non-extrusion welds 222 along the perimeter edge 198. As with the transfer area 212 and transfer valve welds 214, these welds are formed without extrusion of melted plastic into the channel 164 during welding. This advantageously allows complete closure to be obtained. Valve (68 may also be adjustably positioned to provide a restriction, and the welds 222 are accurately formed so that the restriction provided with valve 68 can be accurately accomplished without unwanted leakage. Also, outlet passage 164 is provided with strong welds 226, which create strengthening "beads" as a result of small amounts of extrusion material therealong. These "beads" provide additional mechanical strength but are not in the area 220 where interference with the valve action might have caused a problem. It has been found that the channel areas 216 and 224 can be subject to some of the highest stress in the cassette. There can be relatively high pressure within pumping chamber 158, and the large surface area of sheet 182, which is exposed to the pressure within pumping chamber 158, can pull the areas 216 and 224 which are immediately adjacent to the outlet pumping chamber 158.

Thus, this construction, with increased strength welds 214 and 226 in this area, provides advantages over other constructions, while the valve areas 212 and 220 with non-interfering welds 214 and 222 allow complete transfer valve sealing and complete outlet valve sealing without unwanted leakage.

Referring now to FIG. 15, which is a bottom view of the rigid carrier 180 for use with a single flexible sheet. It will be noted that at the bottom of rigid carrier 180, opposite transfer channel 162 and opposite outlet channel 164, there are indentation areas 228 and 230, respectively. These indentations are formed during the injection molding of rigid carrier 180 and provide advantages according to one embodiment of the welding process by which the special welds 214 and 218 and welds 222 and 226 are formed.

Figure 23:
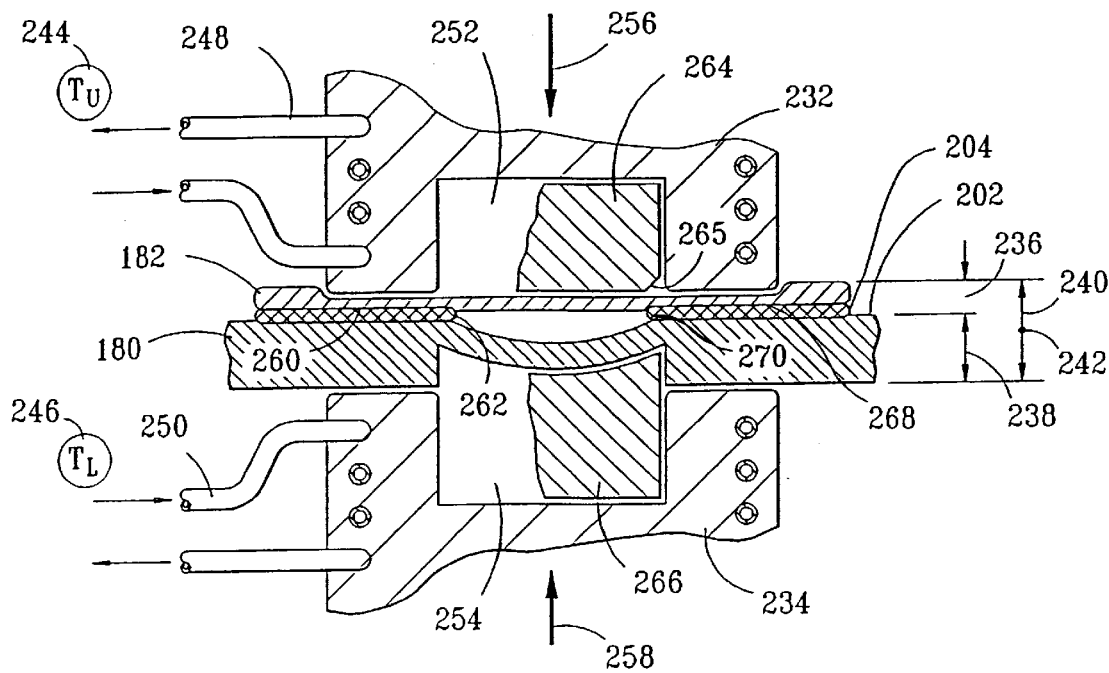
FIG. 23 is a cross-sectional schematic depiction of an RF welding process and apparatus, according to one embodiment of the present invention.
Figure 24:
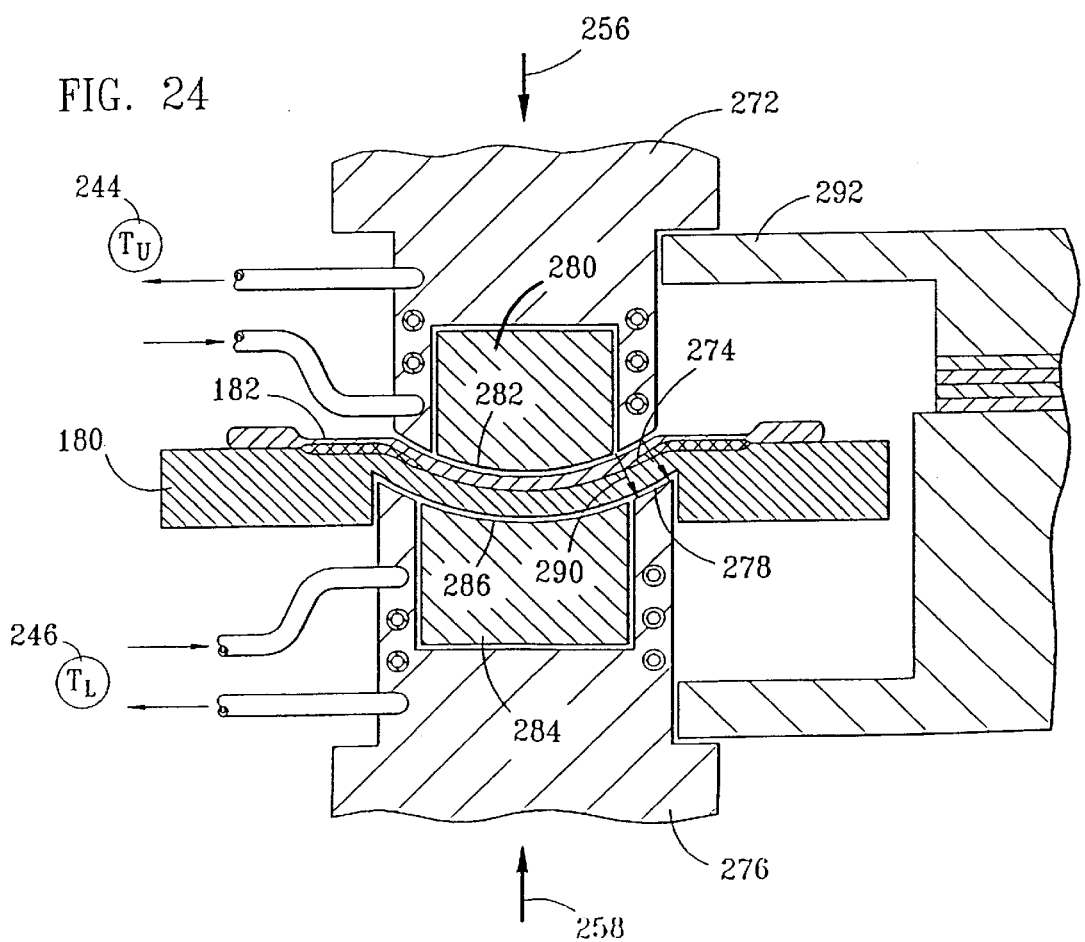
FIG. 24 is a cross-sectional schematic depiction of another part of an RF welding process and apparatus, according to one embodiment of the present invention.

With reference to FIGS. 23 and 24, the special welding method will be more fully explained. FIG. 23 is a schematic depiction of a cross-section of welding dies 232 and 234, shown in operation, welding flexible sheet 182 to the rigid carrier 180. It has been found that with RF welding of a thin sheet 182 having a thickness 236, as for example, 0.0016" (i.e., 1.6 mil), to a rigid carrier 180 having a thickness 238, as for example, 0.80" (i.e., 80 mil), presents difficulties for radio frequency welding. In the RF welding process, the typical result is for the melting of the hottest point generated in the plastic to occur at the midpoint 242, between the entire overall thickness 240, of both pieces of plastic. When the two plastic materials are of the same thickness, the results are satisfactory. However, when a thin sheet is welded to a thicker sheet, then difficulties arise, as all of the melting will occur at the thickest sheet and bonding will not occur at the interface between surface 202 and 204. This problem is further exacerbated by the dissimilarities of the materials, with the thinner sheet being a PVC material and having a particular melting temperature and a particular reactive characteristic to RF signals, and the copolyester of the rigid carrier which has a higher melting temperature and its own characteristic reaction to RF signals. Thus, in order to successfully weld these dissimilar materials, having different thickness, Applicants have uniquely developed a process by which the upper die 232 is preheated to a temperature TU244, and the lower die 234 is heated to a desired temperature TL246. Uniquely and unobviously, the lower die is not heated to a high temperature despite the higher melting temperature of the copolyester and the thickness of the copolyester, but rather the upper die 232 is heated to a temperature TU244, which is higher than the temperature TL246. It was found that this effectively moves the hot point from mid-point 242 up to the interface between surface 202 and surface 204, at a distance 236 from the face of die 232 and at a distance 238 from die 235. Also, in order to avoid welding channel 162 to the film 182, and thereby closing the passage, the die face 232 terminates along each edge of the channel as with the cavity 252. The lower die face also terminates at a corresponding location as to the formation of the cavity 254 in die 234. It was discovered that this arrangement resulted in a weld, as shown schematically at 260, having a projection 262 which extended into the passage. Control of the amount of the extrusion 262 was difficult. In order to facilitate control, a non-conductive spacer 264 was inserted into the cavity 252 and a non-conductive spacer 266 was inserted into the lower cavity 254. These spacers were made of a durable material, such as delrin, which does not conduct and is not effectively melted by the RF electromagnetic signal. Thus, it was found that a weld, such as that schematically depicted at 268, could be formed, having a "bulge" of extruded material 270, which was more readily controlled along a chamfered corner 265 of the upper delrin spacer 264.

The "bulge" 270, nevertheless, was found to potentially interfere with the closure of either valve 62 or valve 64 such that a subsequent welding operation, as shown in FIG. 24, was implemented. In FIG. 24, which is a schematic cross-sectional depiction of the subsequent welding step, an upper die 272 is provided with a radiused surface 274, and a lower die 276 is provided with a concave radiused surface 278. Although previous wisdom for RF welding has been that curved surfaces were nor candidates for RF welding, careful control of the spacing between upper die 272 and lower die 276, rather than careful control of the pressure, was found to be effective to maintain a weld at a curved surface, partially into the radiused channel 162. In this manner, the "bulge" 270 could be effectively flattened to a radius corresponding to that of channel 162, so that the valve could completely seat therealong and have complete closure of the channel 162. A similar process was used with respect to the valve closure at the outlet 164. To further avoid any inadvertent extrusion into the channel, a delrin spacer 280 having a radiused surface 282 was used in the upper die 272, and a delrin spacer 284 having a concave radiused surface 286 was provided in the lower die, thereby effectively damming any extrusion to the compression between film 182 and carrier 180 caused by the compressive pressure between the delrin spacers. In order to maintain appropriate curved surfaces, the distance 190 between the convex die surface 274 and the concave die surface 278 was carefully maintained as with an adjustable mechanical spacer 292, against which the upper die 272 and the lower die 276 abutted during the welding process.

Figure 25:
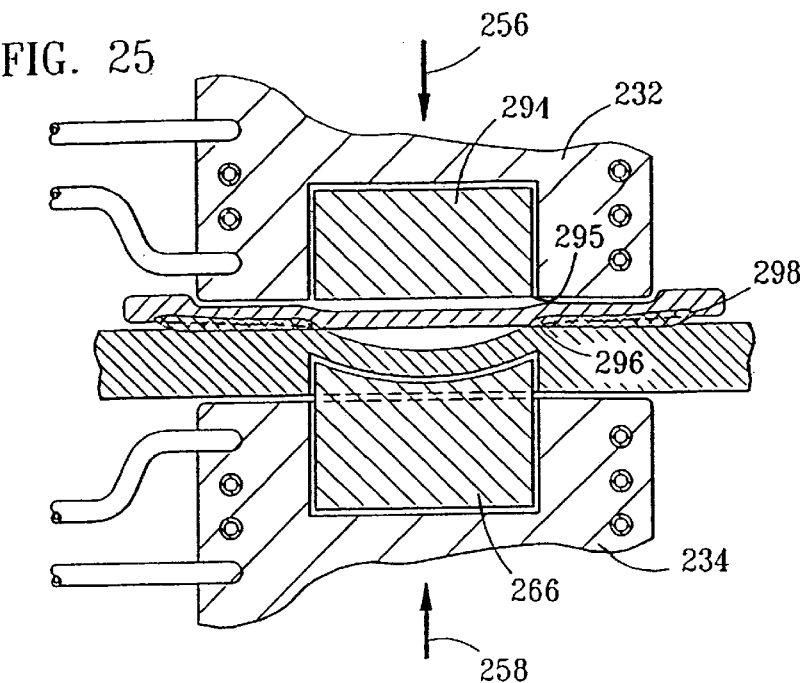
FIG. 25 is a cross-sectional schematic depiction of an alternative preferred RF welding process and apparatus, according to the present invention.
Figure 26:
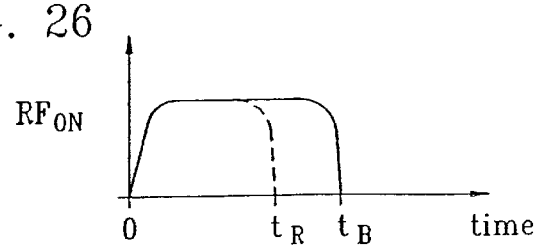
FIG. 26 is a schematic graphical depiction of RF welding time, according to the process of FIG. 25.

Referring now to FIG. 25, a further advantageous preferred method of achieving a weld between a flexible PVC sheet and a rigid carrier of copolyester is schematically depicted. In this embodiment, the upper RF die 232 and the lower die 234 are substantially the same as in the method described with respect to FIG. 23. However, the delrin spacers within cavities 252 and 254 are constructed differently, and the operation of the RF input is also modified. In this instance, the preheating with temperature 244 and 246 is again implemented in order to properly position the "hot" spot, or the weld spot, at the interface between surfaces 204 and 202, as described above with respect to the method depicted in FIG. 23. The tipper delrin insert 294 is provided with square corners 295, extending in the valve contact areas 212 and 242, so that the special welds 214 and 226, which allow complete sealing, are as depicted in FIG. 25. The squaring of the corner 295 did not, in and of itself, result in the weld as depicted, but it was further required to modify the RF on time, as depicted on the graph shown in FIG. 26. The recommended weld time (TR), which previously resulted in a good weld as shown in FIG. 23 at 268, did not successfully cause the weld to flow down along the radius of channel 162, as shown at 296 of FIG. 25. The pressure up to the edge, as provided by corner 295, merely resulted in a damming effect, which caused all of the extrusion to move toward the exterior, as shown at 298. However, increasing the RF weld time to a time (TB), as shown in FIG. 26, caused the corner at the junction between channel 162 and upper surface 202 of the rigid carrier 180, to begin melting, and the compression pressure provided by delrin spacer 294, and particularly, the sharp corner 295 caused the weld to flow radiantly along channel 162. By carefully controlling the increased RF "on" time TB and by maintain proper pressure 256 and 258, a smooth transition weld, as shown at 296, resulted at all welds 214 and 222.

Figure 27:
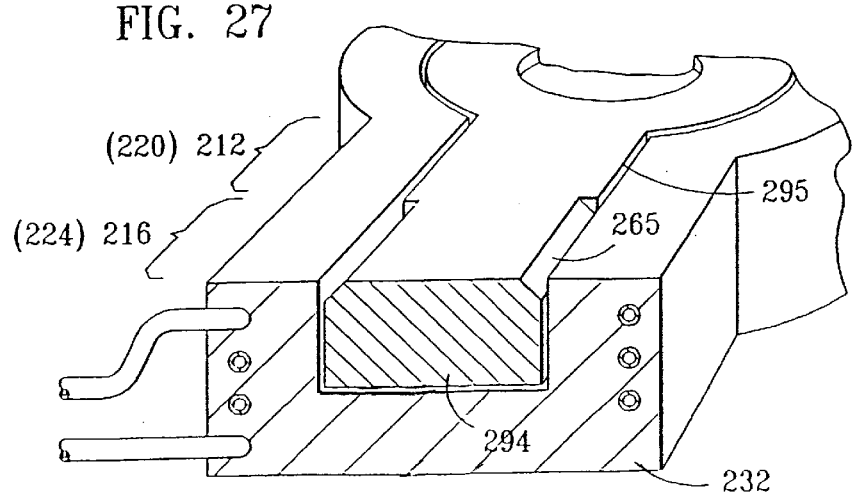
FIG. 27 is a partial perspective view of an upper RF die and delrin insert, according to the method and apparatus of FIG. 25.

With reference to FIG. 27, the modified construction of delrin spacer 294 is depicted in which radiused corners 295 were maintained in the area 216 and 224, where strong welds were required. Thus, weld beads 270, as shown in FIG. 23, and the sharp corners 295 were formed in those valve sealing areas 212 and 220, so that the special welds 214 and 222 resulting, having a configuration as depicted at 296 in FIG. 25.

What is claimed is:

1. A method of welding a flexible PVC sheet to a rigid copolyester carrier that is thicker than said flexible PVC sheet, comprising the steps of:

(a) holding a flat face of a first RF die against said PVC sheet;

(b) holding a flat face of a second RF die against said rigid copolyester carrier;

(c) squeezing a flat surface of said flexible PVC sheet, abutted against a flat surface of said rigid copolyester carried, between said flat faces of said first and second RF dies;

(d) maintaining said first RF die at a first temperature;

(e) maintaining said second RF die at a second temperature, which is lower than said first temperature;

(f) maintaining a predetermined temperature differential between said first and second RF dies, so that a weld plane is established in said flexible PVC sheet and said rigid copolyester carrier between said dies along said flat surfaces of said PVC and said copolyester, which arc being squeezed together;

(g) activating an RF weld signal through said first and second RF dies and said PVC and copolyester therebetween, so that said flexible PVC sheet and said copolyester rigid carrier partially melt and become welded together at said weld plane, established along said abutted surfaces of said PVC sheet and said copolyester rigid carrier;

(h) providing a first cavity in said first RF die formed therein corresponding to an area which is not to be welded;

(i) providing a second cavity in said second RF die corresponding to said area not to be welded;

(j) interposing a non-conductive spacer into said first cavity of said first RF die for bonding said flexible PVC sheet in a desired position at least partially compressed against said rigid copolyester carrier during welding;

(k) forming said non-conductive spacer having a first portion with a square corner terminating immediately adjacent to said area not to be welded along a first short portion thereof; and (l) beveling said non-conductive spacer along a second portion thereof,such that said non-conductive spacer contacts said flexible plastic sheet along a line which is spaced apart from said first RF die in said area not to be welded so that a small weld bead can result partially in said area not to be welded due to reduced compression on said flexible plastic sheet along said beveled second portion of said non-conductive spacer.

* * * * *